United States Patent
Williams et al.

(10) Patent No.: US 9,815,755 B2
(45) Date of Patent: Nov. 14, 2017

(54) METHODS AND APPARATUSES FOR TREATING AN ORGANIC FEED

(71) Applicant: UOP LLC, Des Plaines, IL (US)

(72) Inventors: Chad A. Williams, Arlington Heights, IL (US); Patrick J. Bullen, Elmhurst, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/863,714

(22) Filed: Sep. 24, 2015

(65) Prior Publication Data
US 2016/0090341 A1 Mar. 31, 2016

Related U.S. Application Data
(60) Provisional application No. 62/056,162, filed on Sep. 26, 2014.

(51) Int. Cl.

| | | |
|---|---|---|
| *C10G 19/00* | (2006.01) | |
| *C10G 19/02* | (2006.01) | |
| *C07C 7/00* | (2006.01) | |
| *C07C 7/10* | (2006.01) | |
| *C07C 15/00* | (2006.01) | |
| *C07C 15/40* | (2006.01) | |
| *C07C 15/42* | (2006.01) | |
| *C07C 15/44* | (2006.01) | |
| *B01D 11/00* | (2006.01) | |
| *B01D 11/04* | (2006.01) | |

(52) U.S. Cl.
CPC ............ *C07C 7/10* (2013.01); *B01D 11/04* (2013.01); *B01D 11/0426* (2013.01); *B01D 11/0492* (2013.01)

(58) Field of Classification Search
CPC .. C07C 7/00; C07C 7/10; C07C 15/00; C07C 15/40–15/44; B01D 11/00; B01D 11/04; B01D 11/0426; B01D 11/0492; C10G 19/00; C10G 19/02; C10G 19/073
See application file for complete search history.

(56) References Cited

U.S. PATENT DOCUMENTS

| | | | |
|---|---|---|---|
| RE19,179 E * | 5/1934 | Wheeler et al. ....... | C10G 19/00 196/46 |
| 3,679,765 A | 7/1972 | Houston, Jr. et al. | |
| 4,283,568 A | 8/1981 | Pujado | |
| 4,370,205 A | 1/1983 | Pujado | |
| 5,220,103 A | 6/1993 | Tagamolila et al. | |

OTHER PUBLICATIONS

Sulzer Chemtech, brochures entitled "Separation Technology for the Hydrocarbon Processing Industry" (16 pgs.).
U.S. Appl. No. 14/863,662, filed Sep. 24, 2015.

* cited by examiner

*Primary Examiner* — Natasha Young

(57) ABSTRACT

The present subject matter relates to methods and apparatuses for the continuous preparation of a cumene feed for a cumene oxidation process. More specifically, the subject matter relates to a process for passing a cumene alpha-methylstyrene stream through a caustic wash column having an integrated water wash section for the removal of organic acids.

14 Claims, 1 Drawing Sheet

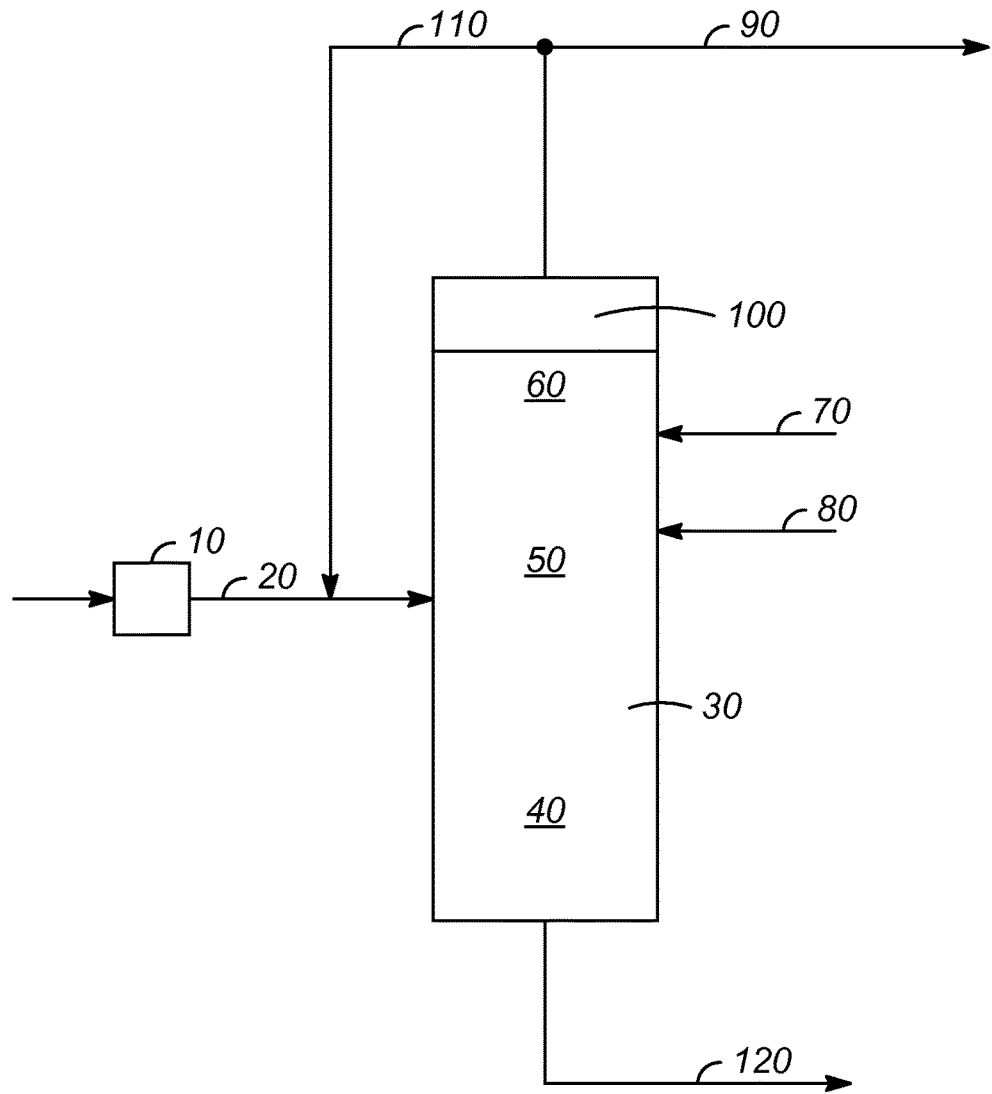

METHODS AND APPARATUSES FOR TREATING AN ORGANIC FEED

CROSS-REFERENCE TO RELATED APPLICATION

This application claims priority from Provisional Application No. 62/056,162 filed Sep. 26, 2014, the contents of which are hereby incorporated by reference

FIELD

The present subject matter relates generally to methods and apparatuses for treating an organic feed. More specifically, the present invention relates to methods for treating a cumene and alpha-methylstyrene stream using a caustic wash column having an integrated water wash section.

BACKGROUND

The present subject matter relates to the preparation of a cumene feed for a cumene oxidation process. More specifically, it relates to a process and apparatus for the preparation of a cumene feed for cumene oxidation from a fresh cumene and alpha-methylstyrene stream. It is important that the caustic wash column is stable. It is also important that caustic does not carry over from the caustic wash column which deactivates the downstream alpha-methylstyrene hydrogenation catalyst. Currently, downstream equipment is used to remove caustic that is carried over from the caustic wash column. For example, a caustic settler may be used after a caustic wash column to ensure the caustic is thoroughly removed from the feed before it enters a downstream unit. However, it would be preferable to improve the caustic wash column itself so that it may be stable and limit the caustic carry over without the need for additional equipment.

Accordingly, it is desirable to develop methods and apparatuses for a process for removing organic acids using an integrated caustic wash column. Furthermore, other desirable features and characteristics of the methods and apparatuses will become apparent from the subsequent detailed description and the appended claims, taken in conjunction with the accompanying drawing and this background.

SUMMARY

Methods and apparatuses for producing hydrocarbons are provided. In an exemplary embodiment, a method includes treating an organic feed using a caustic wash column having an integrated water wash section.

In one approach, a process for treating an organic feed includes a process for treating an organic feed by introducing a feed stream from a feed tank containing at least one organic acid compound into a caustic wash section of a caustic wash column. Then an aqueous caustic scrubbing solution is introduced into the caustic wash column. A water stream is also introduced to a water wash section of the caustic wash column. Contacting of the feed through an aqueous caustic scrubbing solution removes the organic acid from the feed. The process removes spent aqueous caustic and organic acid solution from the caustic wash column. The process also removes an organic product from the water wash section of the caustic wash column having a reduced level of organic acid relative to the feed stream.

In another approach, the apparatus for treating an organic feed includes a caustic wash column having a lower portion, an intermediate portion, and an upper portion. In one example, the line for introducing the feed from a feed tank containing at least one organic acid compound enters the caustic wash column in the intermediate portion of the caustic wash column. A line for introducing an aqueous caustic scrubbing solution is also connected to the caustic wash column. In one example, the line for introducing an aqueous caustic scrubbing solution may enter the caustic wash column in the intermediate portion of the caustic wash column. A line for introducing a water stream into the water wash section of the caustic wash column is connected to the column. In one example, the line for introducing the water stream into the column may enter the column in the upper portion of the column. The column may include jetting trays within the column for contacting of the feed through an aqueous caustic scrubbing solution to remove the organic acid from the feed. A line for removing spent aqueous caustic and organic acid solution from the caustic wash column is connected to the bottom of the column. A line for removing an organic product from the water wash section of the caustic wash column wherein the organic product has a reduced level of organic acid relative to the feed stream is connected the top of the column.

An advantage of the methods and apparatuses for the continuous preparation of a cumene feed is that it provides a more stable system.

Another advantage of the methods and apparatuses for the continuous preparation of a cumene feed is that it limits caustic carry over.

Another advantage of the methods and apparatuses for the continuous preparation of a cumene feed is that it consolidates the amount of units needed to restrict caustic carry over.

A further advantage of the methods and apparatuses for the continuous preparation of a cumene feed is that the feed tank accounts for any upsets from upstream vessels.

Yet another advantage of the methods and apparatuses for the continuous preparation of a cumene feed is that the caustic supplied for the process does not have to be diluted, but can be directly used in the caustic wash column.

Additional objects, advantages and novel features of the examples will be set forth in part in the description which follows, and in part will become apparent to those skilled in the art upon examination of the following description and the accompanying drawing or may be learned by production or operation of the examples. The objects and advantages of the concepts may be realized and attained by means of the methodologies, instrumentalities and combinations particularly pointed out in the appended claims.

BRIEF DESCRIPTION OF THE DRAWING

The FIGURE depicts one or more implementations in accord with the present concepts, by way of example only, not by way of limitations. In the FIGURE, like reference numerals refer to the same or similar elements.

The FIGURE is an illustration of a process for treating an organic feed using a caustic wash column having an integrated water wash section.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The further description of the process of this invention is presented with reference to the attached FIGURE. The FIGURE is a simplified flow diagram of a preferred embodiment of this invention and is not intended as an undue limitation on the generally broad scope of the description provided herein and the appended claims. Certain hardware such as valves, pumps, compressors, heat exchangers, instrumentation and controls, have been omitted as not essential to a clear understanding of the invention. The use and application of this hardware is well within the skill of the art.

The overall process to which this invention pertains concerns the oxidation of a secondary alkylbenzene, for example, isopropylbenzene (cumene) isobutylbenzene, isoamylbenzene, 1-methyl-4-isopropylbenzene, p-diisopropylbenzene, p-diisobutylbenzene, 1-isopropyl-4-isobutylbenzene, cyclohexyl benzene, and the like, to form the corresponding hydroperoxide, i.e., isopropylbenzene hydroperoxide, isobutylbenzene hydroperoxide, isoamylbenzene hydroperoxide, 1-methyl-4-isopropylbenzene hydroperoxide, p-diisopropylbenzene hydroperoxide, p-diisobutylbenzene hydroperoxide, 1-isobutyl-4-isopropylbenzene dihydroperoxide, cyclohexylbenzene hydroperoxide, and the like. The present invention is particularly directed to a process for the preparation of a cumene feed for cumene oxidation from a fresh cumene stream and a recycle cumene stream containing trace quantities of at least one organic acid compound. The organic acid compound is selected from the group consisting of formic acid, acetic acid, benzoic acid, propionic acid, butyric acid and phenol.

The various embodiments described herein relate to methods and apparatuses for treating an organic feed using a caustic wash column having an integrated water wash section. In accordance with the present invention, the vertical, countercurrent contacting zone is preferably contained in a vessel such as a column 30, which has packing, trays or other convenient means to provide countercurrent liquid-liquid extraction. In one example, jetting trays may provide contacting of the organic phase through an aqueous caustic scrubbing solution to remove the organic acid from the organic phase. The contacting zone is preferably operated at a pressure from about atmospheric (0 kPa gauge) to about 150 psig (1035 kPa gauge) and a temperature from about 41° F. (5° C.) to about 140° F. (60° C.). However, other operating temperatures and pressures may be used in the practice of the present process, but preferably so long as the liquid phase is maintained.

Turning to the FIGURE, a feed tank 10 supplies a feed 20 to the caustic wash column 30. In the example shown in the FIGURE, the feed tank 10 ensures that the caustic sufficiently contacts the hydrocarbon mixture because it acts as a place holder for the feed 20, instead of allowing the feed 20 to flow directly from the upstream unit to the caustic wash column 30. The feed 20 in the example shown in the FIGURE includes cumene, alpha-methylstyrene, and phenol. However, it is contemplated that the feed may contain other hydrocarbon mixtures. For example, it is contemplated that the feed may contain acetone, organic acids, benzene, hydroxyacetone, 2-MBF, acetaldehyde, propionaldehyde, and heavy alkyphenols.

The caustic wash column 30 comprises a lower portion 40, an intermediate portion 50, and an upper portion 60. The feed 20 enters the caustic wash column 30 in the intermediate portion 50. The caustic solution 80 enters the caustic wash column 30 in the intermediate portion 50 of the caustic wash column 30. However, it is contemplated that the feed 20 and caustic solution 80 may enter the caustic wash column 30 at other portions of the column 30.

The aqueous caustic solution which is introduced into the caustic/hydrocarbon contacting zone preferably contains from about 1 to about 20 wt % caustic. While various caustic solutions that are known in the art for treating a cumene feed may be used, the preferred caustic solution is an aqueous sodium hydroxide solution. Make-up caustic solutions may have concentrations from about 5 to about 50 wt % caustic. In the example shown in the FIGURE, the sodium hydroxide may comprise 45 wt % of the caustic solution. The concentration of the aqueous caustic solution used is related to the amount of organic acid that is being removed from the feed 20.

A water stream 70 enters the caustic wash column 30 in the upper portion 60 of the column 30. A mesh blanket 100 may also be located in the upper portion 60 of the caustic wash column 30. As the organic feed 20 moves up the caustic wash column 30 the organic acid in the organic feed 20 becomes entrained with the caustic 80 and then is contacted with the water stream 70. Within the column 30, an acid base reaction occurs. The caustic reacts with the phenol to make water and sodium phenate. The organic feed passes through the mesh blanket 100 once before it reaches the top of the column 30. The mesh blanket coalesces any small amounts of water or caustic, therefore minimizing the amount of water exiting the top of the column 30. Once the organic feed reaches the top of the column 30, a clean, mainly caustic free organic phase exits the top of the column 30 in the product stream 90.

A portion of the product stream 90 may be recycled back to the feed 20 via line 110. The recycled product 110 may be admixed with the feed 20 before entering the caustic wash column 30, or the recycled product feed 110 and the feed 20 may enter the caustic wash column 30 at distinct inlets.

A second product stream 120 exits from the bottom of the column 30. The second product stream 120 comprises water, caustic, and sodium phenate.

It should be noted that various changes and modifications to the presently preferred embodiments described herein will be apparent to those skilled in the art. Such changes and modifications may be made without departing from the spirit and scope of the present invention and without diminishing its attendant advantages.

SPECIFIC EMBODIMENTS

While the following is described in conjunction with specific embodiments, it will be understood that this description is intended to illustrate and not limit the scope of the preceding description and the appended claims.

A first embodiment of the invention is an apparatus for treating an organic feed comprising a line for introducing a feed stream from a feed tank containing at least one organic acid compound into a caustic wash section of a caustic wash column; a line for introducing an aqueous caustic scrubbing solution into the caustic wash column; a line for introducing a water stream into a water wash section of the caustic wash column; jetting trays within the column for contacting of the feed through an aqueous caustic scrubbing solution to remove the organic acid from the feed; a line for removing spent aqueous caustic and organic acid solution from the caustic wash column; and a line for removing an organic product from the water wash section of the caustic wash column wherein the organic product has a reduced level of organic acid relative to the feed stream. An embodiment of the invention is one, any or all of prior embodiments in this paragraph up through the first embodiment in this paragraph, wherein the organic feed comprises cumene and alpha-methylstyrene. An embodiment of the invention is one, any or all of prior embodiments in this paragraph up through the first embodiment in this paragraph, wherein the organic acid compound is phenol. An embodiment of the invention is one, any or all of prior embodiments in this paragraph up through the first embodiment in this paragraph, wherein the apparatus removes 10-25 wt % of phenol. An embodiment of the invention is one, any or all of prior embodiments in this paragraph up through the first embodiment in this paragraph, wherein the aqueous caustic scrubbing solution contains sodium hydroxide. An embodiment of the invention is one, any or all of prior embodiments in this paragraph up through the first embodiment in this paragraph, wherein the aqueous scrubbing solution contains 40-50 wt % of sodium hydroxide. An embodiment of the invention is one, any or all of prior embodiments in this paragraph up through the first embodiment in this paragraph, wherein the organic product is a mixture comprising of 75-90 wt % cumene and alpham-ethylstyrene. An embodiment of the invention is one, any or all of prior embodiments in this paragraph up through the first embodiment in this paragraph, wherein the caustic wash column is operated at a pressure from about 0.1 to 3.0 kg/cm2(g) and a temperature from about 30 to 60° C. An embodiment of the invention is one, any or all of prior embodiments in this paragraph up through the first embodiment in this paragraph, further comprising a mesh blanket for coalescing of any water and aqueous caustic scrubbing solution. An embodiment of the invention is one, any or all of prior embodiments in this paragraph up through the first embodiment in this paragraph, further comprising jetting trays for contacting of the organic phase through an aqueous caustic scrubbing solution to remove the organic acid from the organic phase. An embodiment of the invention is one, any or all of prior embodiments in this paragraph up through the first embodiment in this paragraph, wherein the caustic wash section comprises a plurality of trays. An embodiment of the invention is one, any or all of prior embodiments in this paragraph up through the first embodiment in this paragraph, wherein the water wash section comprises a plurality of trays.

A second embodiment of the invention is an apparatus for treating an organic feed comprising a line for introducing a feed stream comprising cumene and alphamethylstyrene from a feed tank into a caustic wash column having a caustic wash section and a water wash section; a line for introducing a scrubbing solution comprising 45 wt % sodium hydroxide into the caustic wash column; a line for introducing a water stream into a water wash section of the caustic wash column; jetting trays within the column for contacting of the feed through an aqueous caustic scrubbing solution to remove the organic acid from the feed; a line for removing water, sodium hydroxide, and sodium phenate from the lower portion of the caustic wash column; and a line for removing 10-25 wt % phenol from the feed. An embodiment of the invention is one, any or all of prior embodiments in this paragraph up through the second embodiment in this paragraph, wherein the caustic wash column is operated at a pressure from about 0.1 to 3.0 kg/cm2(g) and a temperature from about 30 to 60° C. An embodiment of the invention is one, any or all of prior embodiments in this paragraph up through the second embodiment in this paragraph, further comprising a mesh blanket for coalescing of any water and aqueous caustic scrubbing solution. An embodiment of the invention is one, any or all of prior embodiments in this paragraph up through the second embodiment in this paragraph, wherein jetting trays provide contacting of the organic phase through an aqueous caustic scrubbing solution to remove the organic acid from the organic phase. An embodiment of the invention is one, any or all of prior embodiments in this paragraph up through the second embodiment in this paragraph, wherein the caustic wash section comprises a plurality of trays. An embodiment of the invention is one, any or all of prior embodiments in this paragraph up through the second embodiment in this paragraph, wherein the water wash section comprises a plurality of trays.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An apparatus for treating an organic feed comprising:
   a line for introducing a feed stream from a feed tank containing organic feed into a caustic wash section of a caustic wash column, the feed stream comprising cumene, alpha-methylstyrene, and phenol;
   a line for introducing an aqueous caustic scrubbing solution into the caustic wash column;
   a line for introducing a water stream into a water wash section of the caustic wash column;
   jetting trays within the column for contacting of the feed through an aqueous caustic scrubbing solution to remove the phenol from the feed;
   a line for removing spent aqueous caustic and phenol from the caustic wash column; and
   a line for removing an organic product from the water wash section of the caustic wash column wherein the organic product has a reduced level of phenol relative to the feed stream.

2. The apparatus of claim 1, wherein the apparatus removes 10-25 wt % of phenol.

3. The apparatus of claim 1, wherein said aqueous caustic scrubbing solution contains sodium hydroxide.

4. The apparatus of claim 1, wherein the aqueous scrubbing solution contains 40-50 wt % of sodium hydroxide.

5. The apparatus of claim 1, wherein the organic product is a mixture comprising of 75-90 wt % cumene and alpham-ethylstyrene.

6. The apparatus of claim 1, wherein the caustic wash column is operated at a pressure from about 0.1 to 3.0 kg/cm2(g) and a temperature from about 30 to 60° C.

7. The apparatus of claim 1, further comprising a mesh blanket for coalescing of any water and aqueous caustic scrubbing solution.

8. The apparatus of claim 1, wherein the caustic wash section comprises a plurality of trays.

9. The apparatus of claim 1, wherein the water wash section comprises a plurality of trays.

10. An apparatus for treating an organic feed comprising:
    a line for introducing a feed stream from a feed tank into a caustic wash column having a caustic wash section and a water wash section, the feed stream comprising cumene, alpha-methylstyrene and phenol;

a line for introducing a scrubbing solution comprising 45 wt % sodium hydroxide into the caustic wash column;

a line for introducing a water stream into a water wash section of the caustic wash column;

jetting trays within the column for contacting of the feed through an aqueous caustic scrubbing solution to remove the organic acid from the feed;

a line for removing water, sodium hydroxide, and sodium phenate from the lower portion of the caustic wash column; and a line for removing 10-25 wt % phenol from the feed.

11. The apparatus of claim 10, wherein the caustic wash column is operated at a pressure from about 0.1 to 3.0 kg/cm2(g) and a temperature from about 30 to 60° C.

12. The apparatus of claim 10, further comprising a mesh blanket for coalescing of any water and aqueous caustic scrubbing solution.

13. The apparatus of claim 10, wherein the caustic wash section comprises a plurality of trays.

14. The apparatus of claim 10, wherein the water wash section comprises a plurality of trays.

\* \* \* \* \*